United States Patent
Morimoto et al.

(10) Patent No.: US 10,285,631 B2
(45) Date of Patent: May 14, 2019

(54) LIGHT SOURCE DEVICE FOR ENDOSCOPE AND ENDOSCOPE SYSTEM

(71) Applicant: FUJIFILM Corporation, Tokyo (JP)

(72) Inventors: Yoshinori Morimoto, Ashigarakami-gun (JP); Satoshi Ozawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 750 days.

(21) Appl. No.: 14/839,131

(22) Filed: Aug. 28, 2015

(65) Prior Publication Data
US 2016/0058348 A1 Mar. 3, 2016

(30) Foreign Application Priority Data

Aug. 29, 2014 (JP) .................................. 2014-175533

(51) Int. Cl.
*A61B 5/1455* (2006.01)
*A61B 1/00* (2006.01)
(Continued)

(52) U.S. Cl.
CPC ...... *A61B 5/14552* (2013.01); *A61B 1/00165* (2013.01); *A61B 1/0638* (2013.01);
(Continued)

(58) Field of Classification Search
CPC . A61B 1/00009; A61B 1/0638; A61B 5/0059; A61B 5/1455; A61B 5/14551; A61B 5/14552; A61B 5/1459; A61B 1/00165; A61B 1/0052; A61B 1/0661; A61B 5/0031; A61B 5/073; A61B 5/6861
See application file for complete search history.

(56) References Cited

U.S. PATENT DOCUMENTS 5,735,800 A * 4/1998 Yasukawa .......... A61B 5/02438
600/310
2010/0130839 A1* 5/2010 Dowling ............... A61B 5/1459
600/316

(Continued)

FOREIGN PATENT DOCUMENTS

JP 5303012 B2 10/2013
JP 5306447 B2 10/2013

*Primary Examiner* — Eric F Winakur
*Assistant Examiner* — Chu Chuan Liu
(74) *Attorney, Agent, or Firm* — Birch, Stewart, Kolasch & Birch, LLP

(57) ABSTRACT

A band limiter comprises an optical filter, which has first and second filter sections, and a filter moving mechanism for moving the optical filter to place the first or second filter section in a light path of blue light. A passband where transmittance of the first filter section is greater than or equal to half a peak value thereof is defined as a first transmission band. The first transmission band includes a peak wavelength, at which an absorption coefficient of hemoglobin is at its peak. A passband where transmittance of the second filter section is greater than or equal to half a peak value thereof is defined as a second transmission band. The second transmission band does not include an isosbestic wavelength (in the order of 450 nm), at which an absorption coefficient of oxyhemoglobin equals or crosses an absorption coefficient of deoxyhemoglobin.

12 Claims, 13 Drawing Sheets

(51) Int. Cl.
*A61B 5/1459* (2006.01)
*A61B 1/06* (2006.01)
A61B 5/00 (2006.01)
A61B 5/07 (2006.01)

(52) U.S. Cl.
CPC .......... *A61B 1/0669* (2013.01); *A61B 5/1459* (2013.01); *A61B 5/0031* (2013.01); *A61B 5/073* (2013.01); *A61B 5/6861* (2013.01); *A61B 2505/05* (2013.01); *A61B 2562/162* (2013.01)

(56) References Cited

U.S. PATENT DOCUMENTS

| | | |
|---|---|---|
| 2011/0288387 A1 | 11/2011 | Machida et al. |
| 2012/0116192 A1* | 5/2012 | Saito .................. A61B 1/00009 600/323 |
| 2012/0157768 A1 | 6/2012 | Saito |
| 2012/0176486 A1* | 7/2012 | Maeda ............... A61B 1/00009 348/68 |

* cited by examiner

LIGHT SOURCE DEVICE FOR ENDOSCOPE AND ENDOSCOPE SYSTEM

CROSS-REFERENCE TO RELATED APPLICATIONS

The present application claims priority under 35 U.S.C. § 119 to Japanese Patent Application No. 2014-175533, filed Aug. 29, 2014. Each of the above application(s) is hereby expressly incorporated by reference, in its entirety, into the present application.

BACKGROUND OF THE INVENTION

1. Field of the Invention

The present invention relates to a light source device for an endoscope and an endoscope system.

2. Description Related to the Prior Art

In medical fields, diagnoses using endoscope systems are widely performed. The endoscope system comprises a light source device for an endoscope (hereinafter simply referred to as the light source device), an endoscope, and a processor device. The light source device generates illumination light with which an object of interest (hereinafter simply referred to as the object, e.g. mucosa or the like in a body cavity) is to be irradiated. The endoscope system is provided with a normal mode and an oxygen saturation mode. In the normal mode, normal observation using normal illumination light (white light) is performed. In the oxygen saturation mode, various types of observation using special illumination light are performed. The observation of oxygen saturation levels (hereinafter referred to as the oxygen saturation observation) is one of them.

The oxygen saturation observation is a method of observation in which oxygen saturation levels that indicate how much oxygen is contained in blood in blood vessels are calculated and an image representing the oxygen saturation levels is displayed. The oxygen saturation observation is performed by using light (measurement light) whose wavelength range is limited to 450 to 500 nm, in which a difference between the absorption coefficient of oxyhemoglobin and the absorption coefficient of deoxyhemoglobin (in blood vessels) is large (see US2012/0157768 (corresponding to Japanese Pat. No. 5303012)).

In the normal observation, the reduction in contrast (hereinafter referred to as the blood vessel contrast) between the mucosal surface and the blood vessels is prevented by reducing the intensity of a light component in the wavelength range of 460 to 500 nm of normal light (white light) (see US2011/0288387 (corresponding to Japanese Pat. No. 5306447)). This is based on the fact that a difference in reflectance between the blood vessel and the mucosa surrounding the blood vessel is small in the wavelength range greater than or equal to 460 nm. Thereby, the blood vessel contrast in the image is increased.

A broadband light source such as a xenon lamp, a white LED (Light Emitting Diode), or the like is used as the light source device. Recently, a combination of semiconductor light sources of different colors (e.g. a blue LED, a green LED, and a red LED) has been used. With regard to a blue light source, a blue LED having a peak wavelength around 450 to 460 nm is used.

As described in the US2012/0157768 and the US2011/0288387, the illumination light having the wavelength range of 450 to 500 nm is used for the oxygen saturation observation. With regard to the illumination light for the normal observation using an image in which the blood vessel contrast is increased, the intensity of the illumination light in the wavelength range of 460 to 500 nm is reduced. In other words, the blue illumination light for the normal observation differs in wavelength from that for the oxygen saturation observation. For this reason, it is necessary to use different light sources for the normal observation and the oxygen saturation observation, respectively. The two types of observation cannot be performed by using a single endoscope system.

SUMMARY OF THE INVENTION

An object of the present invention is to provide a light source device for endoscope and an endoscope system that allow both of observation of oxygen saturation levels and normal observation using an image in which blood vessel contrast is enhanced.

In order to achieve the above and other objects, an aspect of the present invention provides a light source device (for an endoscope) comprising a blue light source, a first band limiter, a second band limiter, and a band limiter switcher. The blue light source emits blue light having a peak wavelength within a range of 450 to 460 nm. The first band limiter has a first transmission band that is defined as a passband where transmittance of the first band limiter is greater than or equal to half a peak value of the transmittance of the first band limiter. The first transmission band includes a peak wavelength, at which an absorption coefficient of hemoglobin is at a peak. The second band limiter has a second transmission band that is defined as a passband where transmittance of the second band limiter is greater than or equal to half a peak value of the transmittance of the second band limiter. The second transmission band does not include an isosbestic wavelength in the order of 450 nm, at which an absorption coefficient of oxyhemoglobin equals an absorption coefficient of deoxyhemoglobin. The band limiter switcher selectively switches the first band limiter and the second band limiter. The band limiter switcher places the first band limiter in a light path of the blue light to generate first blue light. The band limiter switcher places the second band limiter in the light path of the blue light to generate second blue light.

It is preferred that the first transmission band is on a shorter wavelength side than the second transmission band.

It is preferred that the light source device further comprises an optical filter having the first band limiter and the second band limiter. The band limiter switcher moves the optical filter to place one of the first and second band limiters in the light path of the blue light.

It is preferred that the light source device further comprises a green light source for emitting green light, a red light source for emitting red light, and a light source controller. The light source controller generates first illumination light that contains the first blue light, the green light, and the red light. The light source controller generates second illumination light that contains the second blue light.

An aspect of the present invention provides an endoscope system comprising the above-described light source device for an endoscope, an imaging unit, and an image processing unit. The imaging unit images an object of interest irradiated with the first or second illumination light and outputs an image signal. The image processing unit produces a first image based on the image signal obtained by imaging the object of interest irradiated with the first illumination light. The image processing unit produces a second image based on the image signal obtained by imaging the object of interest irradiated with the second illumination light.

It is preferred that the endoscope system further comprises a display unit for displaying the first image and the second image. It is preferred that the display unit displays the first and second images simultaneously.

It is preferred that the second blue light has a wavelength range in which the absorption coefficient of oxyhemoglobin is greater than the absorption coefficient of deoxyhemoglobin.

It is preferred that the imaging unit has blue pixels for receiving the blue light, green pixels for receiving the green light, and red pixels for receiving the red light.

It is preferred that the image processing unit images the object of interest irradiated with the first illumination light and produces the first image based on a first blue image signal outputted from the blue pixels, a first green image signal outputted from the green pixels, and a first red image signals outputted from the red pixels.

It is preferred that the second illumination light is separated into normal light and measurement light. The normal light contains the second blue light, the green light, and the red light. The measurement light is composed of the second blue light. It is preferred that the image processing unit images the object of interest irradiated with the normal light and produces a base image based on a second blue image signal outputted from the blue pixels, a second green image signal outputted from the green pixels, and a second red image signal outputted from the red pixels. It is preferred that the image processing unit images the object of interest irradiated with the measurement light and calculates the oxygen saturation level based on a third blue image signal outputted from the blue pixels and performs image processing of the base image in accordance with the oxygen saturation level to produce the second image.

It is preferred that the endoscope system further comprises a violet light source for emitting violet light to which the blue pixels are sensitive. It is preferred that the light source controller generates the first illumination light that contains the violet light, the first blue light, the green light, and the red light.

It is preferred that the endoscope system is capable of executing a normal mode in which the object of interest is irradiated only with the first illumination light and only the first image is produced.

According to an aspect of the present invention, an absorption peak wavelength of hemoglobin is included in the first transmission band where the transmittance of the first band limiter is greater than or equal to half the peak value of the transmittance thereof. The isosbestic wavelength (in the order of 450 nm), at which the absorption coefficient of oxyhemoglobin equals (or crosses) the absorption coefficient of deoxyhemoglobin, is not included in the second transmission band where the transmittance of the second band limiter is greater than or equal to half the peak value of the transmittance thereof. The first band limiter and the second band limiter are switched selectively, so that the first or second band limiter is placed in the light path of the blue light. This enables both the normal observation of an image in which the blood vessel contrast is enhanced and the oxygen saturation observation.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
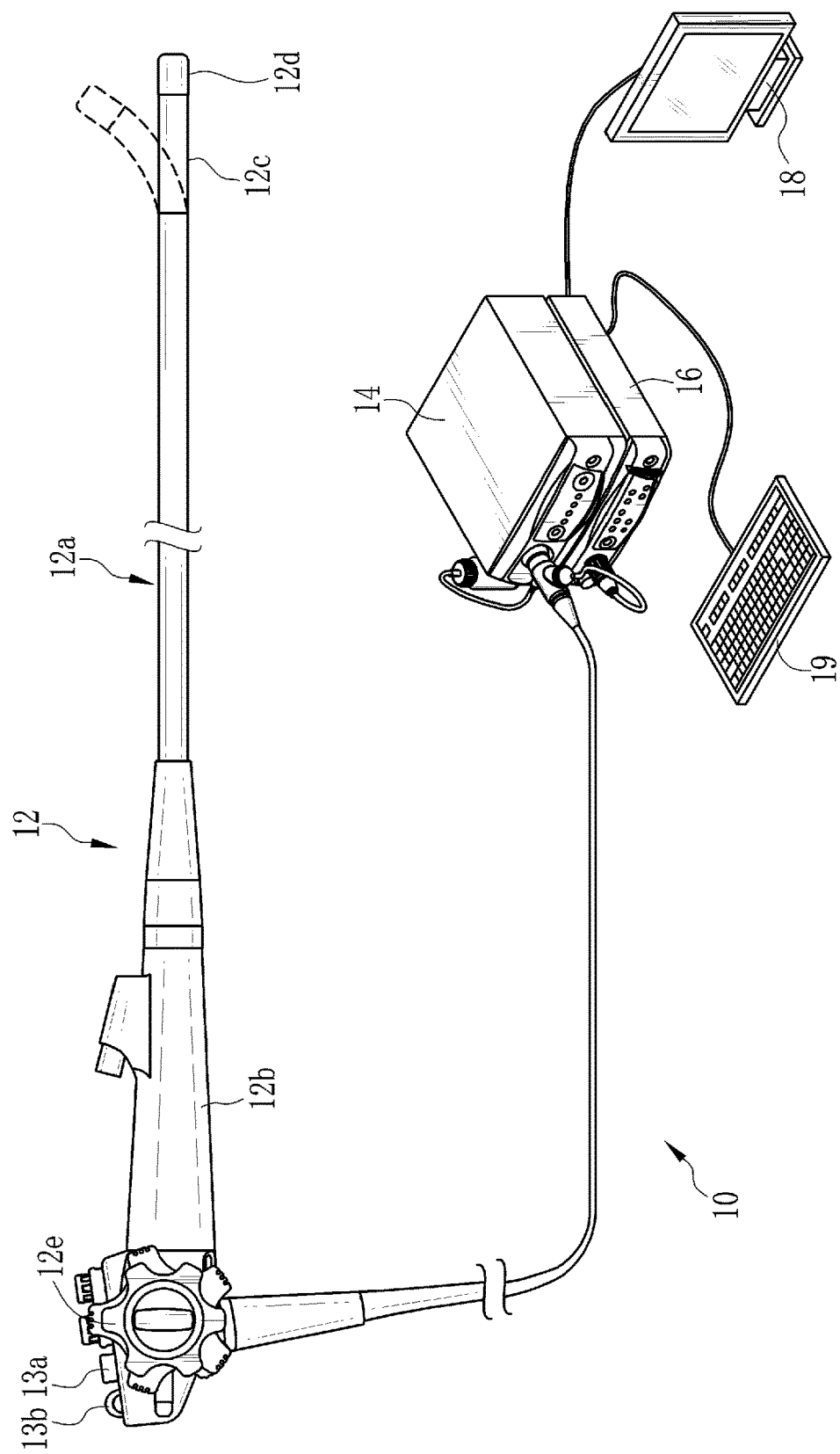
FIG. 1 is an external view of an endoscope system.

In FIG. 1, an endoscope system 10 comprises an endoscope 12, a light source device 14 for an endoscope (hereinafter simply referred to as the light source device) 14, a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e, a mode switch (SW) 13a, and a zoom operating section 13b. The mode SW 13a is operated to switch between observation modes. The endoscope system 10 is capable of executing a normal mode and an oxygen saturation mode.

In the normal mode, a white light image (hereinafter referred to as the normal image), in which the contrast of blood vessels (hereinafter may referred to as the blood vessel contrast) in mucosal surface of living tissue is enhanced, is displayed on the monitor 18 (display unit). In the oxygen saturation mode, an oxygen saturation image is displayed on the monitor 18. The oxygen saturation image refers to an image with colors corresponding to values of the oxygen saturation levels measured by irradiating an object of interest (hereinafter simply referred to as the object) with measurement light. The measurement light has a specific wavelength range for measuring oxygen saturation level (s).

The processor device 16 is electrically connected to the monitor 18 and the console 19. The monitor 18 outputs and displays image (s) and image information and the like associated with the image (s) in each mode. The console 19 functions as a UI (user interface), which receives input operation such as setting a function. Note that an external storage unit (not shown) for recording the images and the image information may be connected to the processor device 16.

Figure 2:
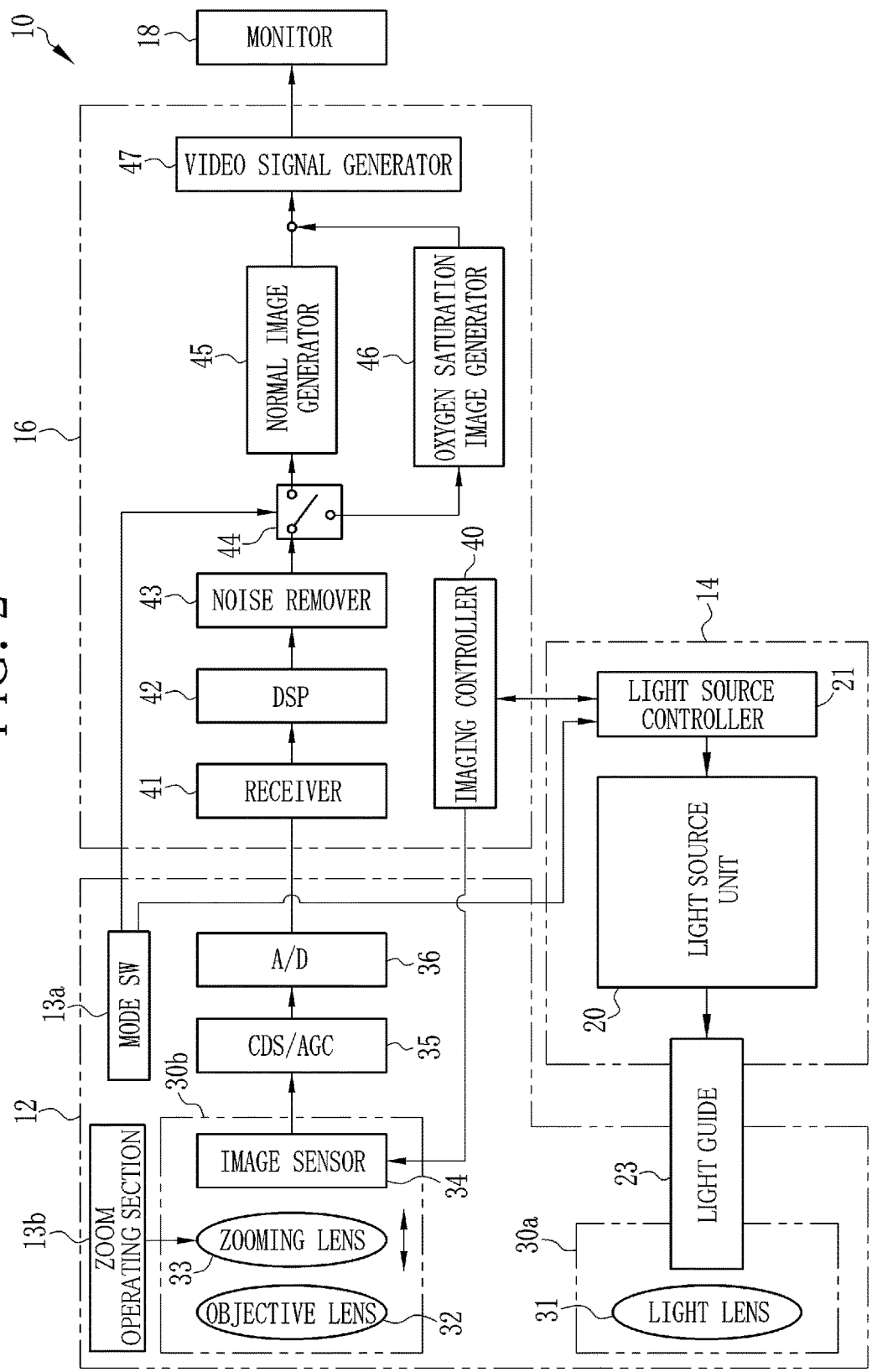
FIG. 2 is a block diagram illustrating functions of an endoscope system.

As illustrated in FIG. 2, the light source device 14 comprises a light source unit 20 and a light source controller 21. The light source unit 20 generates illumination light with which the object is to be irradiated. The light source controller 21 controls the operation of the light source unit 20. The light source unit 20 generates first illumination light in the normal mode and second illumination light in the oxygen saturation mode.

Figure 4:
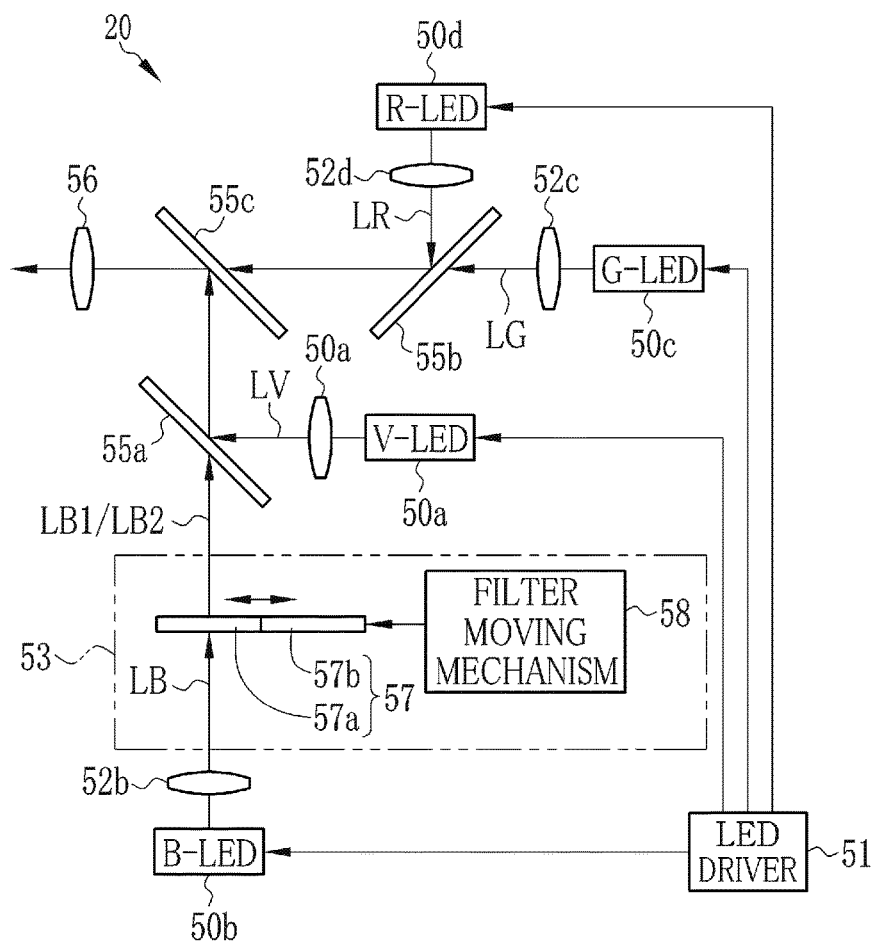
FIG. 4 is a schematic view of a light source device.

The first and second illumination light enters a light guide 23, which extends through the insertion section 12a, through a condenser lens 56 (see FIG. 4). The light guide 23 is incorporated in the endoscope 12 and transmits the first and second illumination light to the distal portion 12d of the endoscope 12. Note that a multimode fiber may be used as the light guide 23. For example, a small-diameter fiber cable with the core diameter 105 μm, the clad diameter 125 μm, and the outer diameter φ 0.3 to 0.5 mm (including a protection layer, being a jacket) may be used.

The distal portion 12d of the endoscope 12 comprises an illumination optical system 30a and an imaging optical system 30b. The illumination optical system 30a has a light lens 31. The first and second illumination light transmitted through the light guide 23 is applied to the object through the light lens 31. The imaging optical system 30b has an objective lens 32, a zooming lens 33, and an image sensor (an imaging unit) 34. The light reflected from the object is incident on the image sensor 34 through the objective lens 32 and the zooming lens 33. Thereby an image of the light reflected from the object is formed on the image sensor 34. Note that the zooming lens 33 is moved as desired between the telephoto end and the wide angle end by operating the zoom operating section 13b, thereby magnifying or reducing the size of the light image of the object formed on the image sensor 34.

The image sensor 34 is a color image sensor. The image sensor 34 captures the light image of the object, and outputs an image signal. It is preferred that the image sensor 34 is a CCD (Charge Coupled Device) image sensor, a CMOS (Complementary Metal-Oxide Semiconductor) image sensor, or the like.

Figure 3:
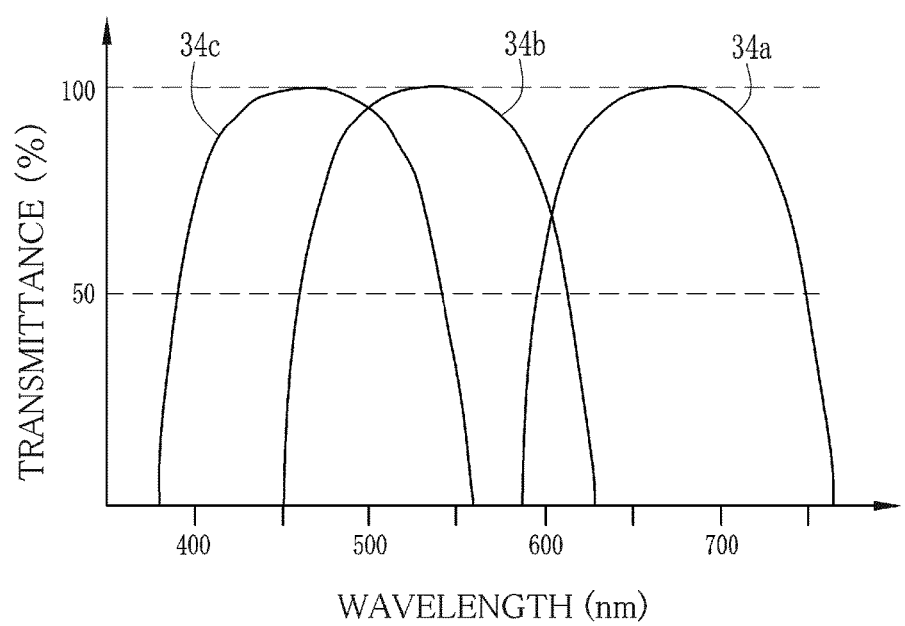
FIG. 3 illustrates spectral characteristics of color filters.

The image sensor 34 comprises red (R) color filters each having first spectral transmittance 34a, green (G) color filters each having second spectral transmittance 34b, and blue (B) color filters each having third spectral transmittance 34c (see FIG. 3). Each pixel is provided with one of the color filters. In other words, the image sensor 34 has R (red) pixels provided with the R color filters, G (green) pixels provided with the G color filters, and B (blue) pixels provided with the B color filters, and outputs RGB image signals. Each pixel is assigned one of RGB color signals to generate the RGB image signals. Note that the B pixels are sensitive to violet light and blue light.

The image signal outputted from the image sensor 34 is transmitted to a CDS/AGC circuit 35. The CDS/AGC circuit 35 performs correlated double sampling (CDS) and automatic gain control (AGC) on the image signal, being an analog signal. The image signal which is outputted from the CDS/AGC circuit 35 is then converted into a digital image signal by an A/D converter 36. The digital image signal is inputted to the processor device 16.

The processor device 16 comprises an imaging controller 40, a receiver 41, a DSP (Digital Signal Processor) 42, a noise remover 43, an image processing selector 44, a normal image generator 45, an oxygen saturation image generator 46, and a video signal generator 47. For example, the normal image generator 45 and the oxygen saturation image generator 46 correspond to an image processor described in claims.

The imaging controller 40 controls timing of imaging the object with the image sensor 34 and timing of outputting the image signals from the image sensor 34. The receiver 41 receives the digital RGB image signals from the endoscope 12. The DSP 42 performs various types of signal processing (defect correction process, offset processing, gain correction process, linear matrix processing, gamma conversion process, demosaicing process, and the like) on the image signal received.

In the defect correction process, signals from defective pixels in the image sensor 34 are corrected. In the offset processing, dark current components are removed from the RGB image signals which have been subjected to the defect correction process. Thereby an accurate zero level is set. In the gain correction process, a signal level is adjusted or corrected by multiplying the RGB image signals that have been subjected to the offset processing, by a specific gain. After the gain correction process, the RGB image signals are subjected to the linear matrix processing to increase color reproducibility. Thereafter, brightness and saturation are adjusted or corrected through the gamma conversion process. After the linear matrix processing, the RGB image signals are subjected to the demosaicing process (also referred to as equalization process or synchronization process) in which color signal(s) lacking in each pixel is generated by interpolation. Owing to the demosaicing process, each pixel has three colors (RGB) of signals.

The DSP 42 performs the demosaicing process and the like on the RGB image signals. Thereafter, the noise remover 43 removes noise from the RGB image signals through a noise removing process (for example, moving average method or median filter method). Then, the RGB image signals are inputted to the image processing selector 44. The image processing selector 44 is controlled by the mode SW 13a. In a case where the mode is set to the normal mode, the image processing selector 44 outputs the RGB image signals to the normal image generator 45. In a case where the mode is set to the oxygen saturation mode, the image processing selector 44 outputs the RGB image signals to the oxygen saturation image generator 46.

The normal image generator 45 operates in, a case where the observation mode is set to the normal mode, and performs a color conversion process, a color enhancement process, and a structure enhancement process on the RGB image signals to produce the normal image (first image). The color conversion process is performed on the RGB image signals through 3×3 matrix processing, a tone conversion process, a three-dimensional LUT process, and the like. The color enhancement process is performed on the RGB image signals which have been subjected to the color conversion process. After the color enhancement process, the RGB image signals are subjected to the structure enhancement process, in which the structure of the object (e.g. surface blood vessels, pit patterns, or the like) is enhanced.

The oxygen saturation image generator 46 operates in a case where the observation mode is set to the oxygen saturation mode. Based on the RGB image signals, the oxygen saturation image generator 46 calculates the oxygen saturation level and produces the oxygen saturation image (second image).

The normal image produced by the normal image generator 45 and the oxygen saturation image produced by the oxygen saturation image generator 46 are inputted to the video signal generator 47. The video signal generator 47 converts each image into a video signal to be displayed on the monitor 18. Based on the video signal inputted from the video signal generator 47, the monitor 18 displays the normal image and/or the oxygen saturation image.

In FIG. 4, the light source unit 20 comprises a V-LED (Violet Light Emitting Diode) 50a, a B-LED (Blue Light Emitting Diode) 50b, a G-LED (Green Light Emitting Diode) 50c, an R-LED (Red Light Emitting Diode) 50d, an LED driver 51, first to fourth collimator lenses 52a to 52d, a band limiter 53, first to third dichroic mirrors (DM) 55a to 55c, and the condenser lens 56.

The V-LED 50a is a violet light source that emits violet light LV having a wavelength range of 380 to 420 nm and the peak wavelength 405 nm. The B-LED 50b is a blue light source that emits blue light LB having a wavelength range of 420 to 500 nm and the peak wavelength 460 nm. The G-LED 50c is a green light source that emits green light LG having a wavelength range of 480 to 600 nm. The R-LED 50d is a red light source that emits red light LR having a wavelength range of 600 to 650 nm and the center wavelength 620-630 nm.

Figure 5:
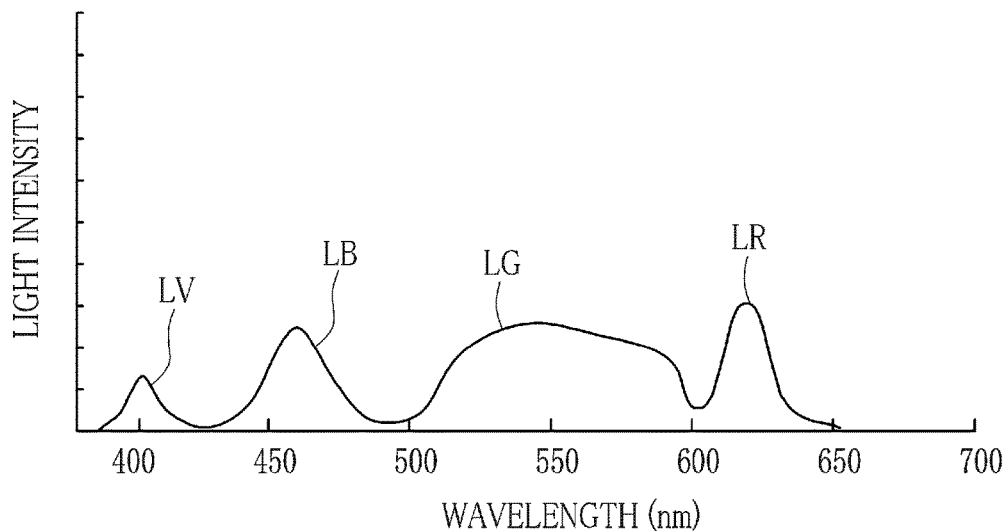
FIG. 5 is a graph illustrating an optical spectrum of violet light, blue light, green light, and red light.

The LED driver 51 independently drives the V-LED 50a, the B-LED 50b, the G-LED 50c, and the R-LED 50d. The emission intensity spectrums of the respective violet light LV, the blue light LB, the green light LG, and the red light LR are distributed as illustrated in FIG. 5. Note that each of the peak wavelengths of the violet light LV and the blue light LB has a wavelength width in the order of ±5 nm to ±10 nm.

The first to fourth collimator lenses 52a to 52d are disposed to correspond to the V-LED 50a, the B-LED 50b, the G-LED 50c, and the R-LED 50d to collimate the violet light LV, the blue light LB, the green light LG, and the red light LR, respectively.

The band limiter 53 comprises an optical filter 57 and a filter moving mechanism 58. The optical filter 57 is disposed in a light path of the blue light LB emitted from the B-LED 50b. To be more specific, the optical filter 57 comprises a first filter section 57a and a second filter section 57b. One of the first filter section 57a and the second filter section 57b is placed in the light path of the blue light LB.

Figure 6:
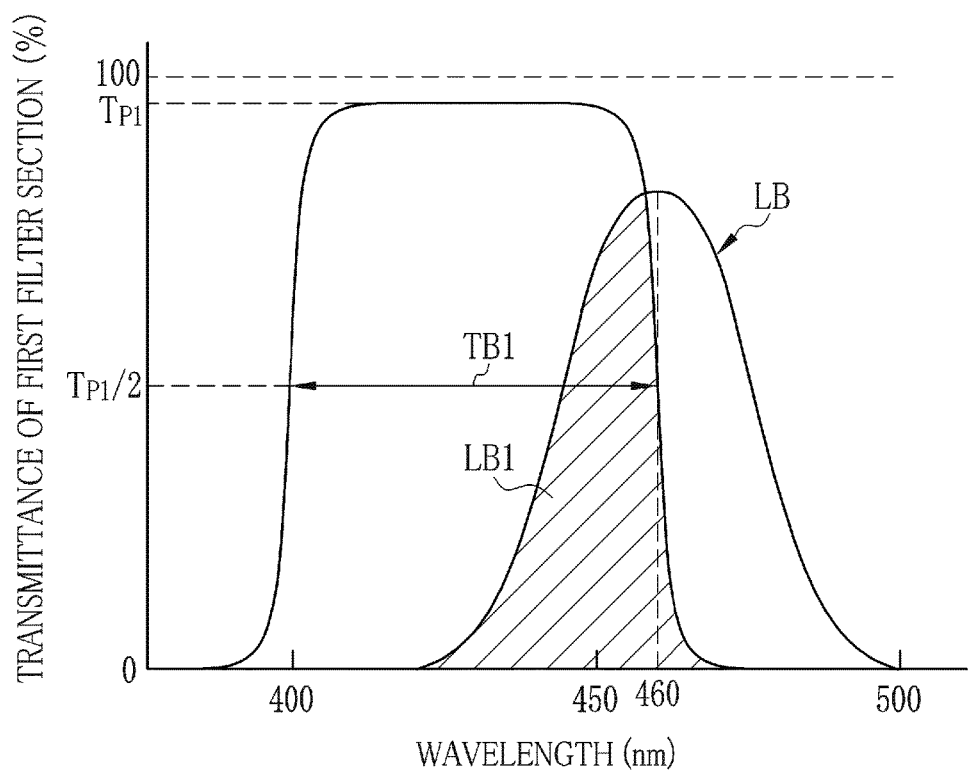
FIG. 6 is a graph illustrating an optical characteristic of a first filter section.
Figure 7:
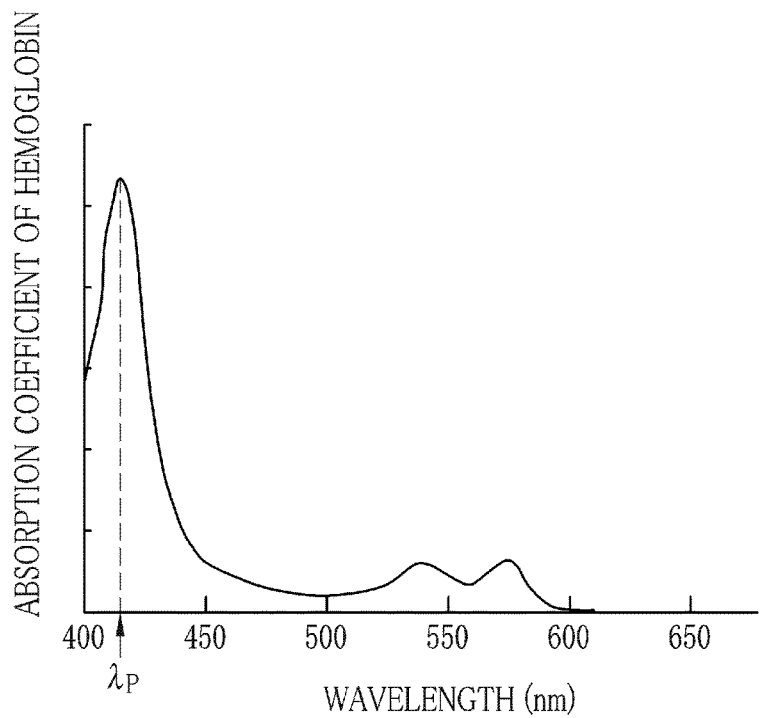
FIG. 7 is a graph illustrating wavelength dependence of an absorption coefficient of hemoglobin.

As illustrated in FIG. 6, the first filter section 57a is a bandpass filter and a peak value $T_{P1}$ of the transmittance is nearly 100%. A passband greater (wider) than or equal to half ($T_{P1}/2$) the peak value $T_{P1}$ is defined as a first transmission band TB1. The first transmission band TB1 is approximately 400 to 460 nm and includes a peak wavelength $\lambda_P$, at which an absorption coefficient of hemoglobin is at its peak, as shown in FIG. 7. The peak wavelength $\lambda_P$ is approximately 415 nm.

The first filter section 57a reduces the intensity of the blue light LB in the wavelength range greater than or equal to in the order of the peak wavelength to generate first blue light LB1 that is a short wavelength component of the blue light LB. The wavelength range of the first blue light LB1 includes the peak wavelength $\lambda_P$, at which the absorption coefficient of hemoglobin is at its peak. For example, the first filter section 57a corresponds to a first band limiter described in the claims.

Figure 8:
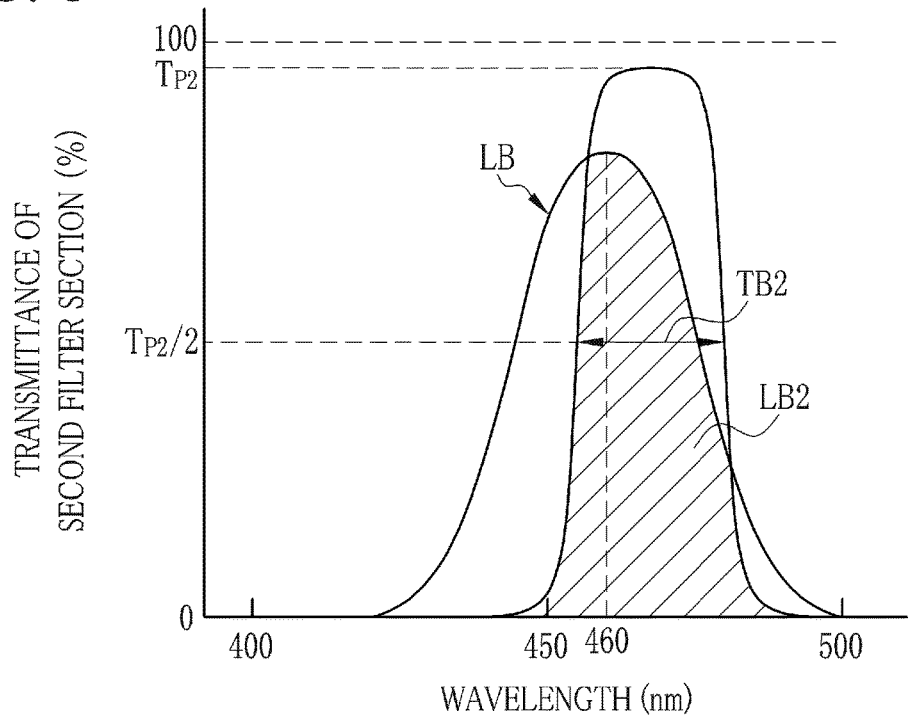
FIG. 8 is a graph illustrating an optical characteristic of a second filter section.

As illustrated in FIG. 8, the second filter section 57b is a bandpass filter and a peak value $T_{P2}$ of the transmittance is nearly 100%. A passband greater (wider) than or equal to half ($T_{P2}/2$) the peak value $T_{P2}$ is defined as a second transmission band TB2. The second transmission band TB2 is approximately 455 to 480 nm and does not include at least an isosbestic wavelength $\lambda_{E2}$ (around 450 nm) (see FIG. 15), which will be described below. The first transmission band TB1 is on a shorter wavelength side than the second transmission band TB2. Note that it is preferred that the second transmission band TB2 does not include any of the isosbestic wavelengths.

The second filter section 57b reduces the intensity of the blue light LB in the wavelength range less than or equal to in the order of the peak wavelength to generate second blue light LB2 that is the long wavelength component of the blue light LB. The wavelength range of the second blue light LB2 does not include the isosbestic wavelength $\lambda_{E2}$ (around 450 nm). For example, the second filter section 57b corresponds to a second band limiter described in the claims.

The filter moving mechanism 58 linearly moves or slides the optical filter 57 in a direction orthogonal to the light path of the blue light LB, thereby placing one of the first filter section 57a and the second filter section 57b in the light path of the blue light LB. The filter moving mechanism 58 selectively switches the filter section placed in the light path of the blue light LB. For example, the filter moving mechanism 58 corresponds to a band limiter switcher described in the claims.

Figure 9:
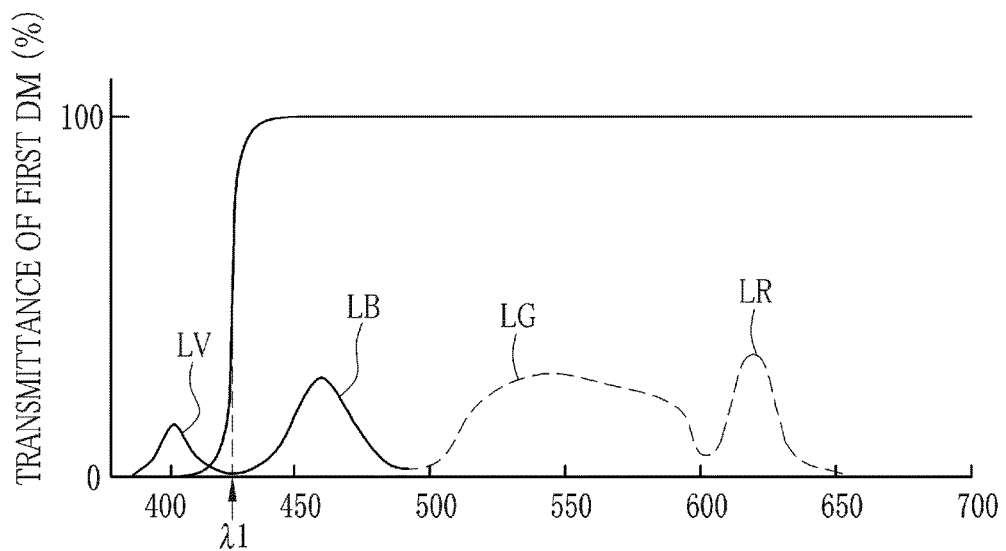
FIG. 9 is a graph illustrating an optical characteristic of a first dichroic mirror.

The light path of the blue light LB (the first blue light LB1 or the second blue light LB2) which has passed through the optical filter 57 is orthogonal to the light path of the violet light LV, and the first DM 55a is disposed at the intersection of the light path of the blue light LB and the light path of the violet light LV. To be more specific, the first DM 55a is disposed such that the first blue light LB1 or the second blue light LB2 is incident on one of its surfaces at an angle of 45° (degrees) and the violet light LV is incident on the other surface at an angle of 45°. As illustrated in FIG. 9, the first DM 55a has a threshold value λ1 of approximately 425 nm, so that the first DM 55a passes the light with the wavelengths longer than the threshold value λ1 and reflects the light with the wavelengths shorter than the threshold value λ1. Thereby, the first DM 55a combines the light path of the blue light LB which has passed the optical filter 57 with the light path of the violet light LV.

Figure 10:
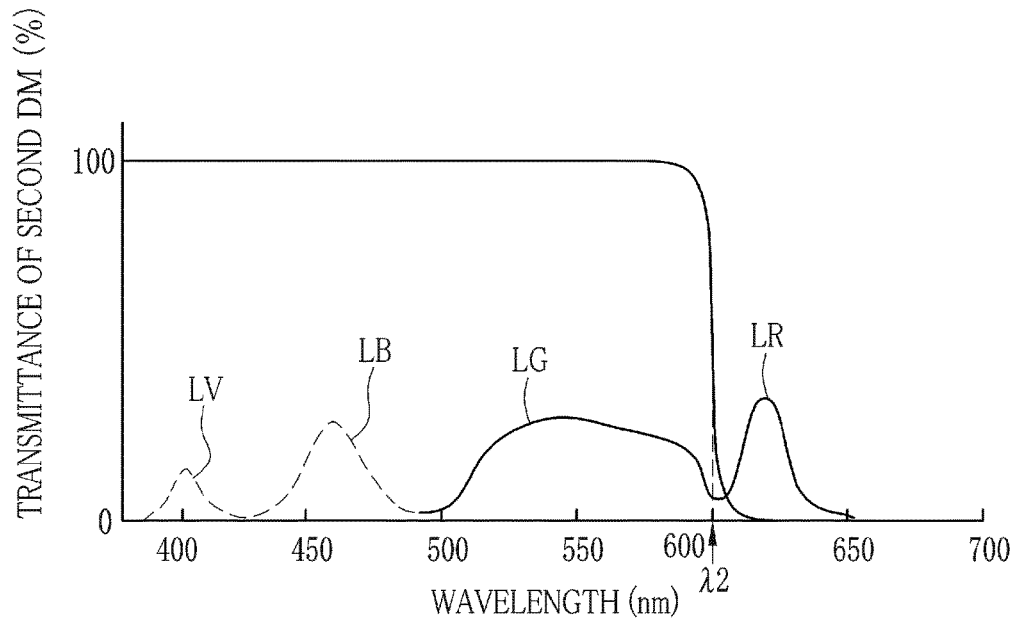
FIG. 10 is a graph illustrating an optical characteristic of a second dichroic mirror.

The light path of the green light LG emitted from the G-LED 50c is orthogonal to the light path of the red light LR emitted from the R-LED 50d, and the second DM 55b is disposed at the intersection of the light paths of the green light LG and the red light LR. To be more specific, the second DM 55b is disposed such that the green light LG is incident on one of its surfaces at an angle of 45° and the red light LR is incident on the other surface at an angle of 45°. As illustrated in FIG. 10, the second DM 55b has a threshold value λ2 of approximately 600 nm, so that the second DM 55b passes the light with the wavelengths shorter than the threshold value λ2 and reflects the light with the wavelengths longer than the threshold value λ2. Thereby, the second DM 55*b* combines the light path of the green light LG with the light path of the red light LR.

Figure 11:
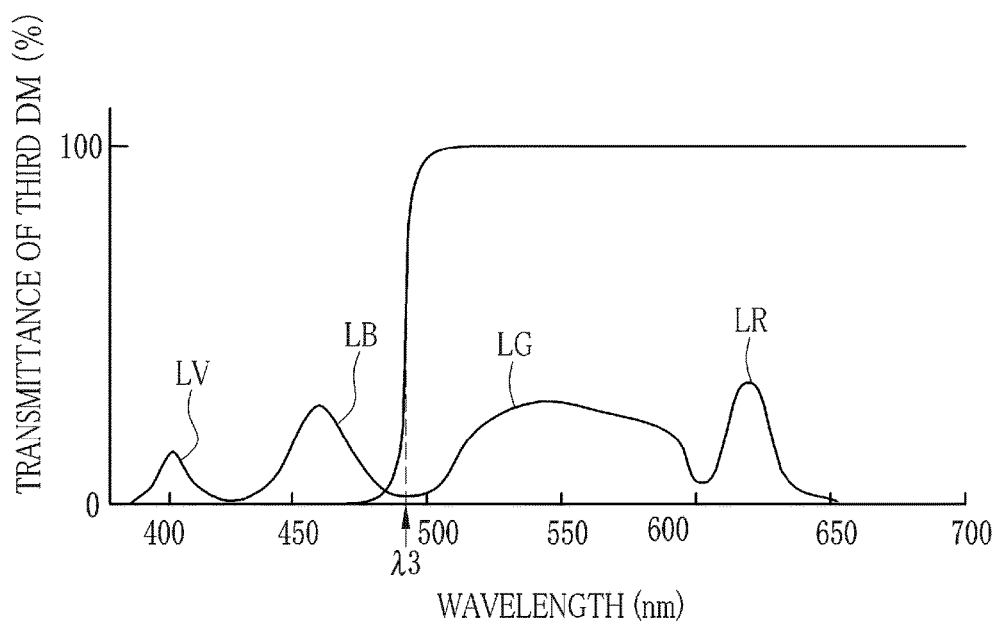
FIG. 11 is a graph illustrating an optical characteristic of a third dichroic mirror.

The light path of the blue light LB (the first blue light LB1 or the second blue light LB2) and the violet light LV, which have been combined together by the first DM 55*a*, is orthogonal to the light path of the green light LG and the red light LR, which have been combined together by the second DM 55*b*, and the third DM 55*c* is disposed at the intersection thereof. To be more specific, the third DM 55*c* is disposed such that the blue light LB and the violet light LV are incident on one of its surfaces at an angle of 45° and the green light LG and the red light LR are incident on the other surface at an angle of 45°. As illustrated in FIG. 11, the third DM 55*c* has a threshold value λ3 of approximately 490 nm, so that third DM 55*c* passes the light with the wavelengths longer than the threshold value λ3 and reflects the light with the wavelengths shorter than the threshold value λ3. Thereby, the third DM 55*c* combines the light path of the blue light LB and the violet light LV with the light path of the green light LG and the red light LR.

The condenser lens 56 is disposed at the close proximity of an incident end of the light guide 23. The condenser lens 56 collects the light from the third DM 55*c* and allows the collected light to enter the incident end of the light guide 23.

The LED driver 51 and the filter moving mechanism 58 are controlled by the light source controller 21 in accordance with the observation mode chosen. To be more specific, in the normal mode, the light source controller 21 controls the filter moving mechanism 58 to place the first filter section 57*a* of the optical filter 57 in the light path of the blue light LB. The light source controller 21 controls the LED driver 51 to turn on all of the V-LED 50*a*, the B-LED 50*b*, the G-LED 50*c*, and the R-LED 50*d*.

Figure 12:
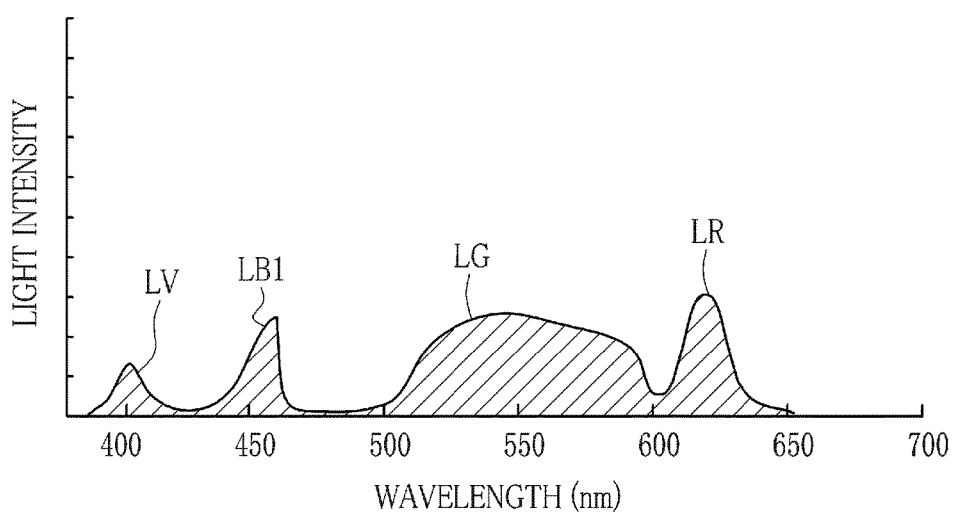
FIG. 12 is a graph illustrating an optical spectrum of first illumination light.

Thereby, in the normal mode, the light source unit 20 emits the first illumination light having a light intensity spectrum illustrated in FIG. 12. The first illumination light enters the light guide 23 through the condenser lens 56. The first illumination light is substantially the white light. As described above, in the normal mode, the first filter section 57*a* limits the wavelength range (or band) of the blue light LB to generate the first blue light LB1 because the light in the wavelength range of 460 to 500 nm reduces the contrast of the structure such as surface blood vessels, pit patterns, and the like.

The first filter section 57*a* has the first transmission band TB1 of approximately 400 to 460 nm, so that the intensity of the wavelengths greater than or equal to approximately 460 nm of the blue light LB is reduced. Actually, the lower limit of the wavelength range whose intensity is to be reduced has a wavelength width in the order of 5 to 10 nm. In order to maintain color rendering properties of the xenon light source, it is preferred that a discrete wavelength range does not exist in the optical spectrum of the illumination light applied to the object. For this reason, the first filter section 57*a* does not reduce the intensity of the light in the wavelength range greater than or equal to 460 nm to zero, but reduces the intensity of the light in the wavelength range greater than or equal to 460 nm such that the color rendering properties of the xenon light source is maintained. Therefore, as illustrated in FIG. 12, a discrete wavelength range does not exist in the first illumination light.

In the oxygen saturation mode, the light source controller 21 allows the light source unit 20 to emit the second illumination light. The second illumination light is separated into normal light and measurement light. In the oxygen saturation mode, the light source controller 21 controls the filter moving mechanism 58 to place the second filter section 57*b* of the optical filter 57 in the light path of the blue light LB and allows alternately executing a first emission mode, in which the normal light is emitted, and a second emission mode, in which the measurement light is emitted.

In the first emission mode, the second filter section 57*b* of the optical filter 57 is placed in the light path of the blue light LB and all of the V-LED 50*a*, the B-LED 50*b*, the G-LED 50*c*, and the R-LED 50*d* are turned on. In the normal mode, the normal light having the light intensity spectrum (see FIG. 13) is emitted from the light source unit 20 and enters the light guide 23 through the condenser lens 56.

Figure 14:
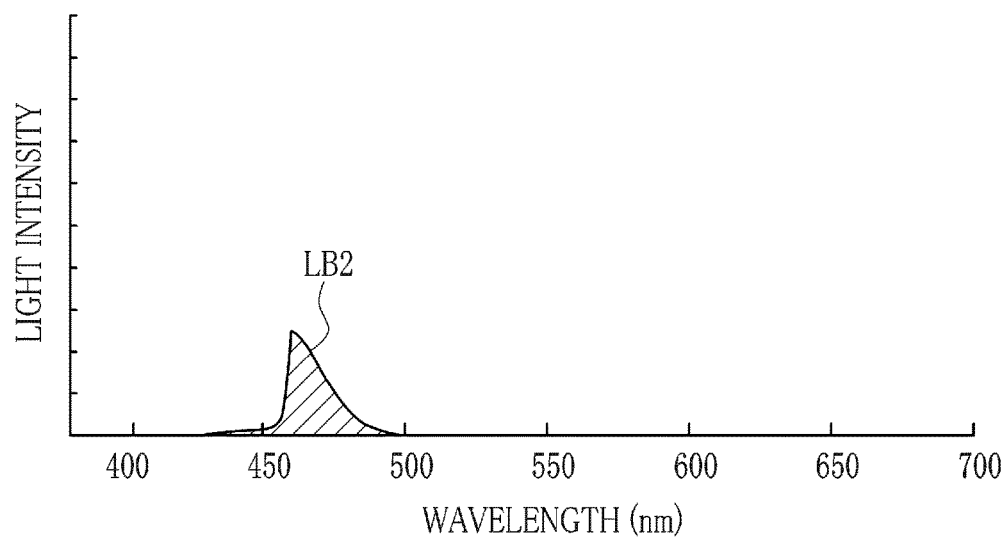
FIG. 14 is a graph illustrating an optical spectrum of measurement light of the second illumination light.

The second emission mode is used to measure the oxygen saturation level(s). In the second emission mode, the light source controller 21 controls the LED driver 51 to turn on the B-LED 50*b* and turn off the V-LED 50*a*, the G-LED 50*c*, and the R-LED 50*d* while the second filter section 57*b* of the optical filter 57 is placed in the light path of the blue light LB. Thereby, in the second emission mode, the measurement light having the light intensity spectrum illustrated in FIG. 14 is emitted from the light source unit 20 and enters the light guide 23 through the condenser lens 56.

As described above, in the normal mode, the first illumination light is applied to the object. The B pixels of the image sensor 34 receive the violet light LV and the first blue light LB1 which are reflected from the object, and output the B image signal. The G pixels of the image sensor 34 receive the green light LG reflected from the object, and output the G image signal. The R pixels of the image sensor 34 receive the red light LR reflected from the object, and output the R image signal. Hereinafter, the B image signal, the G image signal, and the R image signal obtained in the normal mode are referred to as the first blue image signal (B1 image signal), the first green image signal (the G1 image signal), and the first red image signal (the R1 image signal).

In the oxygen saturation mode, the second illumination light is applied to the object. To be more specific, in the first emission mode of the oxygen saturation mode, the normal light is applied to the object. The B pixels of the image sensor 34 receive the violet light LV and the second blue light LB2 which are reflected from the object, and output the B image signal. The G pixels of the image sensor 34 receive the green light LG reflected from the object, and output the G image signal. The R pixels of the image sensor 34 receive the red light LR reflected from the object, and output the R image signal. Hereinafter, the B image signal, the G image signal, and the R image signal in the first emission mode are referred to as the second blue image signal (B2 image signal), the second green image signal (G2 image signal), and the second red image signal (R2 image signal).

In the second emission mode in the oxygen saturation mode, the measurement light is applied to the object. The measurement light is composed of the second blue light LB2. The B pixels of the image sensor 34 receive the second blue light LB2 reflected from the object, and output the B image signal. Hereinafter, the B image signal obtained in the second emission mode is referred to as the third blue image signal (B3 image signal). Note that the image sensor 34 is also capable of outputting the G and R image signals in the second emission mode. However, the G and R image signals are not used for calculating the oxygen saturation level and producing the oxygen saturation image. In this embodiment, the image sensor 34 outputs only the B3 image signal in the second emission mode.

The second blue light LB2 has a specific wavelength range for measuring the oxygen saturation level(s). The specific wavelength range refers to a wavelength range in which a difference between the absorption coefficient of oxyhemoglobin and the absorption coefficient of deoxyhemoglobin causes a difference in amount of light absorption in accordance with the oxygen saturation level.

Figure 15:
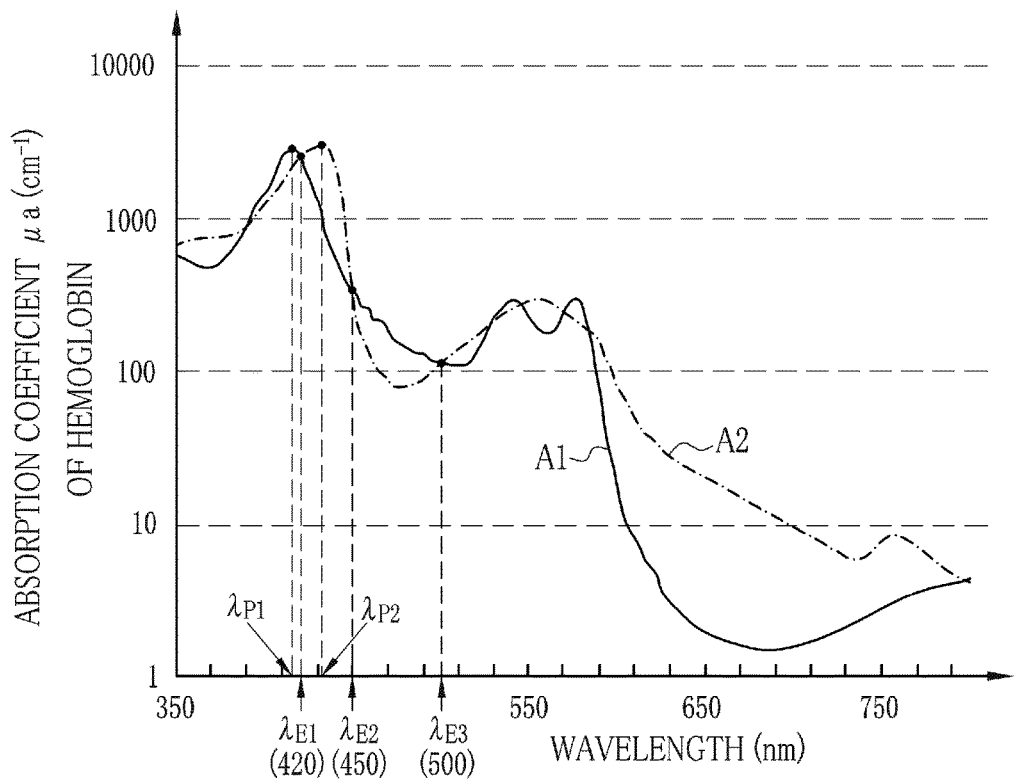
FIG. 15 is a graph illustrating the wavelength dependence of the absorption coefficients of oxyhemoglobin and deoxyhemoglobin.

As illustrated in FIG. 15, a magnitude relationship between an absorption coefficient A1 of oxyhemoglobin and an absorption coefficient A2 of deoxyhemoglobin varies depending on a wavelength range, and the absorption coefficient A1 of oxyhemoglobin equals (or crosses) the absorption coefficient A2 of deoxyhemoglobin at two or more isosbestic points (or isosbestic wavelengths). The wavelength at which the absorption coefficient A1 of oxyhemoglobin equals (or crosses) the absorption coefficient A2 of deoxyhemoglobin is referred to as the isosbestic wavelength. For example, there are first to third isosbestic wavelengths $\lambda_{E1}$ to $\lambda_{E3}$ in a wavelength range from violet to blue. The first to third isosbestic wavelengths $\lambda_{E1}$ to $\lambda_{E3}$ are approximately 420 nm, approximately 450 nm, and approximately 500 nm, respectively. A relationship A2>A1 is satisfied in a wavelength range (420 to 450 nm) between the first isosbestic wavelength $\lambda_{E1}$ and the second isosbestic wavelength $\lambda_{E2}$. A relationship A1>A2 is satisfied in a wavelength range (450 to 500 nm) between the second isosbestic wavelength $\lambda_{E2}$ and the third isosbestic wavelength $\lambda_{E3}$.

The second transmission band TB2 is approximately 455 to 480 nm and lies between the second isosbestic wavelength $\lambda_{E2}$ and the third isosbestic wavelength $\lambda_{E3}$ and does not include any of the isosbestic wavelengths. The second blue light LB2 passing through (or within) the second transmission band TB2 does not include any of the isosbestic wavelengths. In other words, the difference between the absorption coefficient A1 of oxyhemoglobin and the absorption coefficient A2 of deoxyhemoglobin is large enough to measure the oxygen saturation level. Thus, the second blue light LB2 is suitable for the measurement light for measuring the oxygen saturation level.

On the other hand, the first blue light LB1 passing through (or within) the first transmission band TB1 (approximately 400 to 460 nm) includes the second isosbestic wavelength $\lambda_{E2}$, so that the first blue light LB1 is not suitable for the measurement light for measuring the oxygen saturation level. However, the first blue light LB1 has a wavelength range which includes the peak wavelength $\lambda_{P1}$, at which the absorption coefficient A1 of oxyhemoglobin is at its peak, and the peak wavelength $\lambda_{P2}$, at which the absorption coefficient A2 of deoxyhemoglobin is at its peak, and is likely to be absorbed by the oxyhemoglobin and the deoxyhemoglobin. Therefore the first blue light LB1 contributes to the improvement of the contrast of the surface blood vessels in the image.

In the oxygen saturation mode, the imaging controller 40 receives a synchronization signal from the light source controller 21 (or inputs a synchronization signal to the light source controller 21). Thereby the imaging controller 40 synchronizes the imaging operation of the image sensor 34 with each of emission period of the normal light and emission period of the measurement light. To be more specific, in a first emission period, in which the normal light is emitted from the light source unit 20, the imaging controller 40 allows the image sensor 34 to take an image of the object irradiated with the normal light and to output the B2 image signal, the G2 image signal, and the R2 image signal. In a second emission period, in which the measurement light is emitted from the light source unit 20, the imaging controller 40 allows the image sensor 34 to take an image of the object irradiated with the measurement light and to output the B3 image signal.

Figure 16:
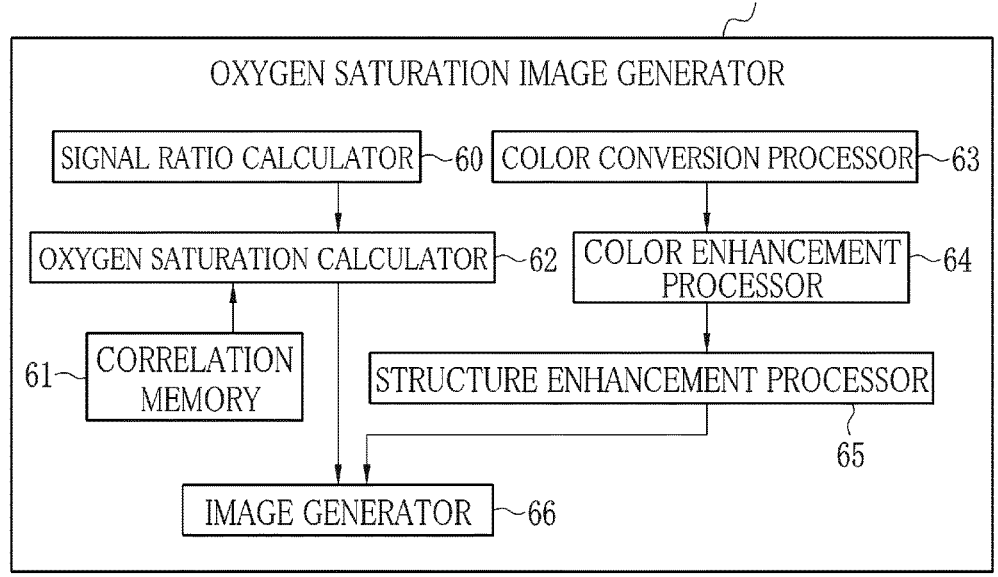
FIG. 16 is a block diagram illustrating functions of an oxygen saturation image generator.

In FIG. 16, the oxygen saturation image generator 46 comprises a signal ratio calculator 60, a correlation memory 61, an oxygen saturation calculator 62, a color conversion processor 63, a color enhancement processor 64, a structure enhancement processor 65, and an image generator 66.

The signal ratio calculator 60 calculates a signal ratio, which is used by the oxygen saturation calculator 62 to calculate the oxygen saturation level. To be more specific, the signal ratio calculator 60 calculates a ratio (hereinafter referred to as the first signal ratio B3/G2) between the B3 image signal and the G2 image signal, for each pixel. The B3 image signal is obtained by imaging the object in the second emission mode. The G2 image signal is obtained by imaging the object in the first emission mode. The signal ratio calculator 60 also calculates a ratio (hereinafter referred to as the second signal ratio R2/G2) between the R2 image signal and G2 image signal, which are obtained by imaging the object in the first emission mode, for each pixel.

Figure 17:
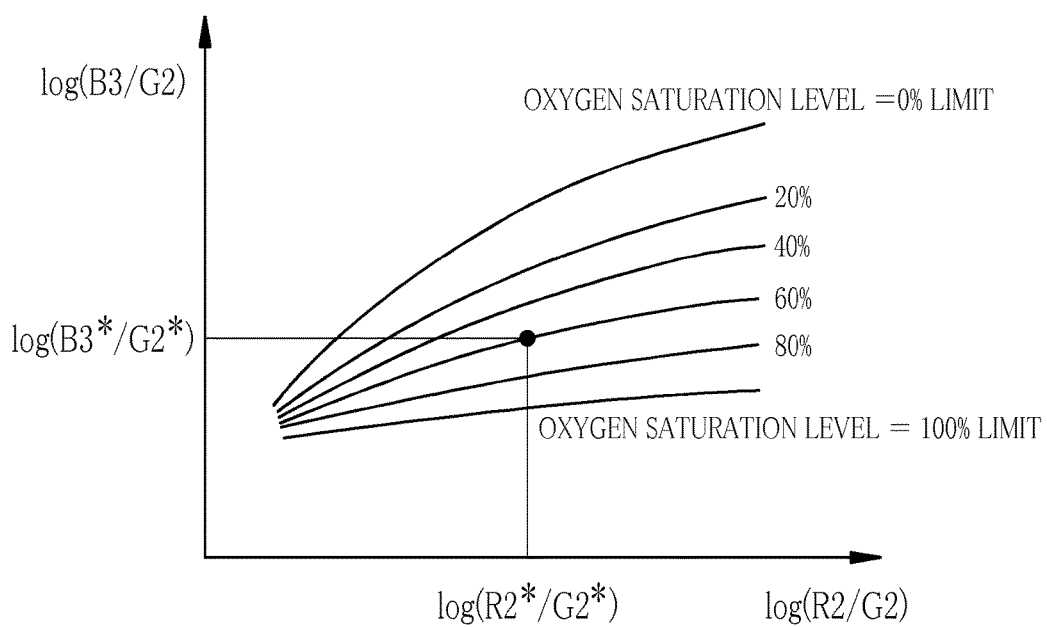
FIG. 17 is a graph illustrating a correlation between signal ratio and oxygen saturation level.

The correlation memory 61 stores a correlation between each signal ratio calculated by the signal ratio calculator 60 and the oxygen saturation level. The correlation is stored in a form of a two-dimensional table, which defines contour lines (or isolines) of the oxygen saturation levels in a two-dimensional space (see FIG. 17). The positions and shapes of the contour lines with respect to the signal ratios are obtained in advance based on physical simulations of light scattering. An interval between the contour lines varies with the second signal ratio R2/G2 that represents the blood volume. Note that the correlation between the signal ratio and the oxygen saturation level is stored in log scale.

The correlation is closely related to absorption characteristics (see FIG. 15) and light scattering characteristics of the oxyhemoglobin and the deoxyhemoglobin. It is easy to obtain the information of the oxygen saturation level with the use of the second blue light LB2 having the wavelength range in which the difference between the absorption coefficient of oxyhemoglobin and the absorption coefficient of deoxyhemoglobin is large. However, the B3 image signal obtained from the second blue light LB2 is highly dependent not only on the oxygen saturation level but also on the blood volume. For this reason, the oxygen saturation level is calculated accurately by using the second signal ratio R2/G2 in addition to the B3 image signal. The second signal ratio R2/G2 is obtained from the G2 image signal, which varies depending mostly on the blood volume, and the R2 image signal, which has low dependence on the oxygen saturation level and the blood volume.

The oxygen saturation calculator 62 refers to the correlation stored in the correlation memory 61 and calculates the oxygen saturation level which corresponds to the first signal ratio B3/G2 and the second signal ratio R2/G2 that are calculated by the signal ratio calculator 60. For example, in the case of the first signal ratio B3*/G2* and the second signal ratio R2*/G2* (see FIG. 17), the oxygen saturation level calculated is "60%".

Note that it is very rare that the first signal ratio B3/G2 or the second signal ratio R2/G2 is calculated to be an extremely large or small value. To be more specific, in FIG. 17, it is very rare that the coordinates represented by the first signal ratio B3/G2 and the second signal ratio R2/G2 are greater than the lower limit contour line that indicates 0% oxygen saturation level, or less than the upper limit contour line that indicates the 100% oxygen saturation level. However, as a precaution, the oxygen saturation calculator 62 outputs that the oxygen saturation level is 0% in case the calculated oxygen saturation level is less than 0%, and outputs that the oxygen saturation is 100% in case the calculated oxygen saturation level exceeds 100%.

As described above, the oxygen saturation image generator 46 calculates the oxygen saturation level with the use of the signal ratio calculator 60, the correlation memory 61, and the oxygen saturation calculator 62. The oxygen saturation image generator 46 also produces an image (hereinafter referred to as the base image), from which the oxygen saturation image is produced, with the use of the color conversion processor 63, the color enhancement processor 64, and the structure enhancement processor 65.

The color conversion processor 63 performs a color conversion process on the B2 image signal, the G2 image signal, and the R2 image signal, which are obtained by imaging the object in the first emission mode, through 3×3 matrix processing, a tone conversion process, a three-dimensional LUT process, and the like. After the color conversion process, the color enhancement processor 64 performs the color enhancement process on the B2 image signal, the G2 image signal, and the R2 image signal. After the color enhancement process, the structure enhancement processor 65 performs the structure enhancement process on the B2 image signal, the G2 image signal, and the R2 image signal. The structure enhancement process enhances the structure (e.g. the surface blood vessels and pit patterns) of the object. In other words, the base image is produced from the B2 image signal, the G2 image signal, and the R2 image signal that have been subjected to the various types of image processing similar to those performed by the normal image generator 45.

The image generator 66 produces the oxygen saturation image, which shows the oxygen saturation level of the object, with the use of the oxygen saturation level calculated by the oxygen saturation calculator 62 and the B2 image signal, the G2 image signal, and the R2 image signal that have been subjected to the above-described various types of image processing. To be more specific, the image generator 66 multiplies each of the B2 image signal, the G2 image signal, and the R2 image signal by a gain in accordance with the oxygen saturation level, for each pixel (hereinafter referred to as the gain process).

For example, with regard to the pixel with the oxygen saturation level of 60% or more, the image generator 66 sets the gain for the B2 image signal, the G2 image signal, and the R2 image signal to "1". This means that the image generator 66 does not perform the gain process. With regard to the pixel with the oxygen saturation level of less than 60%, the gain for the B2 image signal is set to be less than "1" and the gain for the G2 image signal and the R2 image signal is set to be greater than or equal to "1" in accordance with the oxygen saturation level. The oxygen saturation image is produced by using the B2 image signal, the G2 image signal, and the R2 image signal that are obtained after the gain process. For this reason, in the oxygen saturation image, the pixel with a high oxygen level (the pixel with the oxygen saturation level of 60 to 100%) is expressed in a color similar to that of the normal image. The pixel with a low oxygen level (the pixel with the oxygen saturation level of less than 60%) is expressed in a color (pseudo color) different from that of the normal image.

In this embodiment, note that the image generator 66 performs the gain process, in accordance with the oxygen saturation level, only on the pixels with low oxygen levels. Instead, the gain process may also be performed on the pixels with high oxygen levels. Thereby the entire oxygen saturation image is displayed in pseudo-colors. The reference value of the oxygen saturation level that separates the high and low oxygen levels is set to 60% by way of example. The reference value may be changed as necessary.

Figure 18:
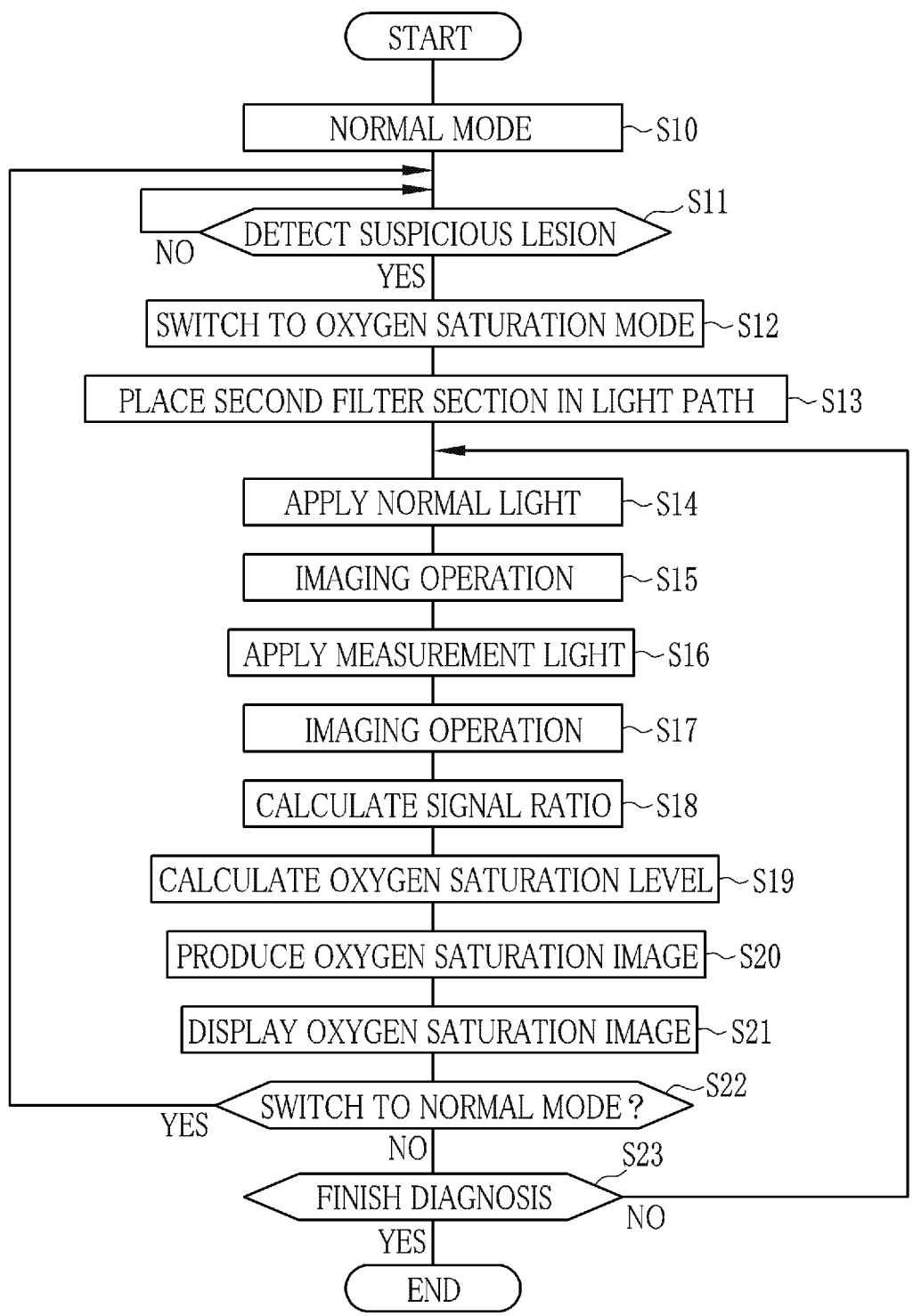
FIG. 18 is a flowchart illustrating an operation of the endoscope system.

Hereinafter, referring to a flowchart illustrated in FIG. 18, an operation of this embodiment is described. First, in the normal mode, screening from distant view is performed (S10). In the normal mode, the first filter section 57a of the optical filter 57 is placed in the light path of the blue light LB. In a case where a suspicious lesion, being a site suspected to be a lesion such as a brownish area or redness, is detected during the screening (S11), the zoom operating section 13b is operated to zoom (magnify) the object including the suspicious lesion. Also, the mode SW 13a is operated to switch from the normal mode to the oxygen saturation mode (S12).

Upon the observation mode is switched to the oxygen saturation mode, the light source controller 21 places the second filter section 57b of the optical filter 57 in the light path of the blue light LB (S13). The light source controller 21 turns on all of the V-LED 50a, the B-LED 50b, the G-LED 50c, and the R-LED 50d. Thereby the normal light composed of the violet light LV, the second blue light LB2, the green light LG, and the red light LR, is applied to the object (S14). The image sensor 34 takes an image of the object irradiated with the normal light and outputs the B2 image signal, the G2 image signal, and the R2 image signal (S15).

Thereafter, the light source controller 21 automatically switches the emission mode and turns on only the B-LED 50b. Thereby the measurement light composed of the second blue light LB2 is applied to the object (S16). The image sensor 34 takes an image of the object irradiated with the measurement light and outputs the B3 image signal (S17).

Upon obtaining the B2 image signal, the G2 image signal, and the R2 image signal in the first emission mode and the B3 image signal in the second emission mode, the oxygen saturation image generator 46 calculates the first signal ratio B3/G2 and the second signal ratio R2/G2 (S18) with the use of the signal ratio calculator 60 and calculates the oxygen saturation level (S19) with the use of the oxygen saturation calculator 62. Based on the B2 image signal, the G2 image signal, and the R2 image signal, the oxygen saturation image generator 46 generates the base image, from which the oxygen saturation image is produced, with the use of the color conversion processor 63, the color enhancement processor 64, and the structure enhancement processor 65.

The image generator 66 multiplies each of the B2 image signal, the G2 image signal, and the R2 image signal that have been subjected to the various types of image processing, by a gain in accordance with the oxygen saturation level and thereby produces the oxygen saturation image (S20). The oxygen saturation image is converted into a video signal by the video signal generator 47, and then displayed on the monitor 18 (S21).

The steps S14 to S21 in the oxygen saturation mode are repeated until the oxygen saturation mode is switched to the normal mode (YES in S22) or the diagnosis is finished (YES in S23).

Note that the above steps are described by way of example. The observation and the diagnosis in the oxygen saturation mode may be performed in a different manner. For example, in the above-described steps, the object is observed in a close view in the oxygen saturation mode by way of example. The oxygen saturation mode may be chosen to perform the screening from the distant view. In the above embodiment, an image of the object is taken in the second emission mode after an image of the object is taken in the first emission mode. Alternatively, the image is taken in the first emission mode after the image is taken in the second emission mode.

As described above, the first blue light LB1 and the second blue light LB2 are selectively generated based on the blue light LB emitted from the B-LED 50*b*, allowing various types of observation (or examinations) and diagnoses. In the normal mode, the first blue light LB1, in which the intensity of the wavelength component greater than or equal to 460 nm is reduced out of the blue light LB, is used. Thereby, a blue image component, in which the blood vessel contrast is improved, is obtained with high image quality. In the oxygen saturation mode, the second blue light LB2, in which the intensity of the wavelength component less than or equal to 460 nm is reduced out of the blue light LB, is used as the measurement light. Thereby, the oxygen saturation level is calculated with high accuracy.

Note that, in the above embodiment, the peak wavelength of the blue light LB is 460 nm, but not limited thereto. However, it is preferred that the peak wavelength of the blue light LB is greater than or equal to 450 nm and it is more preferred that the peak wavelength of the blue light LB is within a range of 450 to 460 nm.

It is preferred that the intensity of the wavelength component at least greater than or equal to the peak wavelength of the blue light LB is reduced to generate the first blue light LB1. It is preferred that the intensity of the wavelength component at least less than or equal to the peak wavelength of the blue light LB is reduced to generate the second blue light LB2.

In the above embodiment, the first filter section 57*a* and the second filter section 57*b* are bandpass filters. The first filter section 57*a* may be a high frequency pass filter, which passes light in a wavelength range less than or equal to a specific wavelength (approximately 460 nm). The second filter section 57*b* may be a low frequency pass filter, which passes light in a wavelength range greater than or equal to a specific wavelength (approximately 460 nm).

Note that, in the above embodiment, the band limiter 53 allows the filter moving mechanism 58 to linearly move (or slide) the optical filter 57, thereby switching the filter (the first filter section 57*a* or the second filter section 57*b*) placed in the light path of the blue light LB. Alternatively, the optical filter 57 may be a rotary plate formed with the semicircular first filter section 57*a* and the semicircular second filter section 57*b*. The filter section to be placed in the light path of the blue light LB is switched by rotating the rotary plate.

In the above embodiment, the first to third DMs 55*a* to 55*c* with the optical characteristics illustrated in FIGS. 9 to 11 are used but are not limited thereto. The optical characteristics (transmissive and reflective characteristics) of each of the first to third DMs 55*a* to 55*c* may be reversed.

In the above embodiment, the image sensor 34 is a primary color image sensor. Instead, a complementary color image sensor with complementary color filters of C (cyan), M (magenta), Y (yellow), and G (green) may be used. The complementary color image sensor outputs CMYG image signals, which are converted into the RGB image signals through a color conversion process. A monochrome image sensor may be used instead. In this case, the V-LED 50*a*, the B-LED 50*b*, the G-LED 50*c*, and the R-LED 50*d* are turned on in a time-division manner. In this case, note that the V-LED 50*a* and the B-LED 50*b* may be turned on simultaneously.

Figure 19:
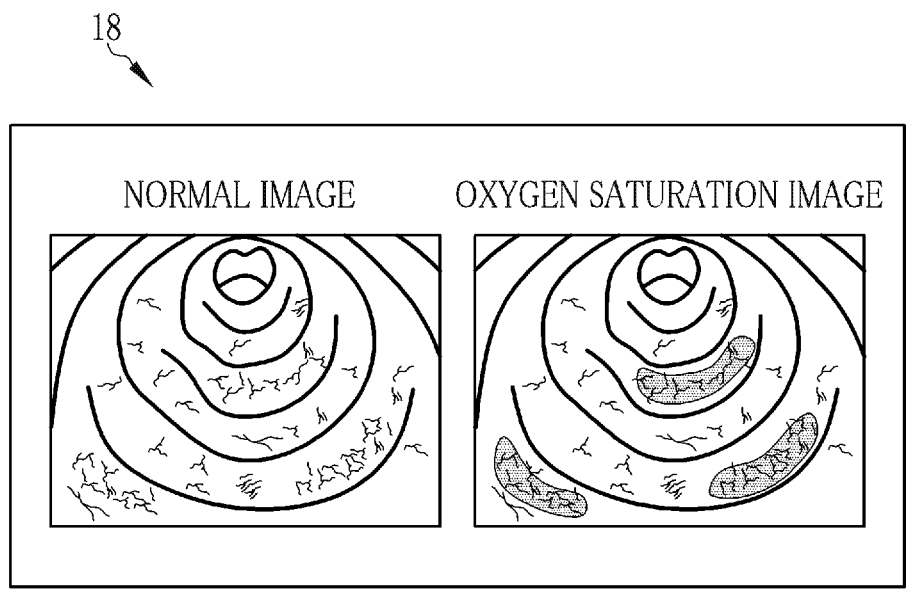
FIG. 19 illustrates images displayed on a monitor by way of example.

In the above embodiment, the monitor 18 displays a normal image in the normal mode and an oxygen saturation image in the oxygen saturation mode. As illustrated in FIG. 19, the monitor 18 may display the normal image (the first image) in addition to the oxygen saturation image (the second image) in the oxygen saturation mode. The simultaneous display of the normal image and the oxygen saturation image on the monitor 18 allows checking the original image (the normal image) of the low oxygen saturation image having the portions colored differently in accordance with the values of the oxygen saturation levels.

In the second emission mode in the above embodiment, the B-LED 50*b* is turned on while the V-LED 50*a*, the G-LED 50*c*, and the R-LED 50*d* are turned off. Instead of turning them off, the amounts of the light may be reduced to extremely small values to the extent that substantially only the blue light LB is emitted. Thus, occurrence of switching noise of the LEDs is prevented by not completely turning off the V-LED 50*a*, the G-LED 50*c*, and the R-LED 50*d*.

Figure 13:
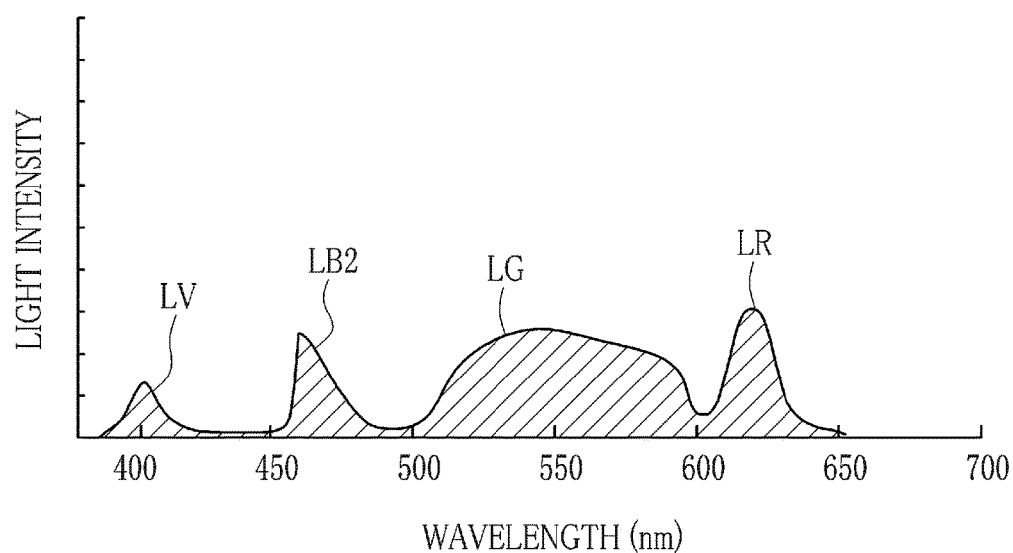
FIG. 13 is a graph illustrating an optical spectrum of normal light of second illumination light.

In the above embodiment, the normal light having the light intensity spectrum shown in FIG. 13 is used as the illumination light in the first emission mode of the oxygen saturation mode. Instead, the normal light having the light intensity spectrum shown in FIG. 12 may be used. In this case, the first blue light LB1 is generated in the first emission mode. The second blue light LB2 is generated in the second emission mode.

In the above embodiment, the optical filter 57 is moved in accordance with switching the emission mode. To be more specific, in the first emission mode, the first filter section 57*a* is placed in the light path of the blue light LB. Thereby the first blue light LB1 is generated. In the second emission mode, the second filter section 57*b* is placed in the light path of the blue light LB. Thereby the second blue light LB2 is generated.

The first blue light LB1 is generated in the first emission mode, so that the normal light, in which the intensity of the light in the wavelength range of 460 to 500 nm is reduced, is used to produce a base image, which is used for producing an oxygen saturation image. Thereby the contrast of the fine structure such as the surface blood vessels and the pit patterns is improved in the image. The oxygen saturation image is produced based on the base image with high image quality and improved blood vessel contrast.

In the above embodiment, the endoscope system has the normal mode and the oxygen saturation mode. In addition, it is preferred that the endoscope system is provided with a blue-light mode, in which intensities of short wavelength components of the first illumination light are enhanced. In the blue-light mode, the light emission intensities of the V-LED 50*a* and the B-LED 50*b* are increased to be higher than those in the normal mode, to generate the first illumination light in which the intensities of the short wavelength components are increased. Other than that, the configuration is similar to that in the above embodiment. The violet light LV and the first blue light LB1 contained in the first illumination light are likely to be absorbed by hemoglobin in the blood vessels in the mucosal surface. For this reason, the surface blood vessels and the pit patterns are further enhanced in an image.

In the above embodiment, the light source device 14 and the processor device 16 are provided separately. Alternatively, the light source device and the processor device may be provided integrally.

Figure 20:
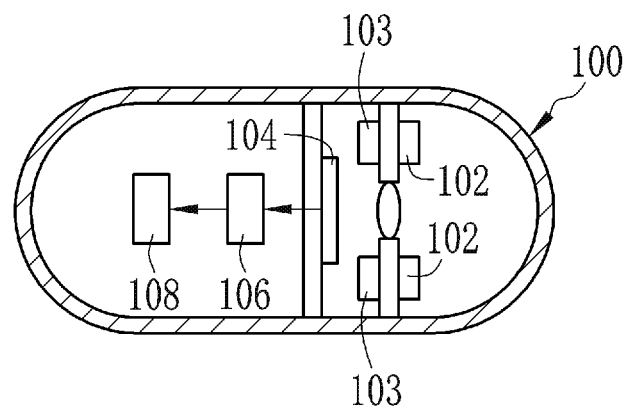
FIG. 20 is a schematic view of a capsule endoscope.

In the above embodiment, an aspect of the present invention is performed using the endoscope system 10 comprising the endoscope 12 provided with the image sensor 34. The observation or examination is performed by inserting the endoscope 12 into a body cavity. The present invention is also suitable for a capsule endoscope system. For example, as illustrated in FIG. 20, the capsule endoscope system comprises at least a capsule endoscope 100 and a processor device (not shown).

The capsule endoscope 100 comprises a light source 102, a light source controller 103, an image sensor 104, an oxygen saturation image generator 106, and a transmission/reception antenna 108. The light source 102 comprises a V-LED that emits the violet light LV, a B-LED that emits the blue light LB, a G-LED that emits the green light LG, and an R-LED that emits the red light LR, and a band limiter for selectively generating the first blue light LB1 and the second blue light LB2 from the blue light LB. The light source 102 corresponds to the light source unit of the above embodiment.

The light source controller 103 controls the light source 102, in a manner similar to the light source controller 21 of the above embodiment. The light source controller 103 is wirelessly communicable with the processor device of the capsule endoscope system through the transmission/reception antenna 108. The processor device of the capsule endoscope system is substantially similar to the processor device 16 of the above embodiment, except that the oxygen saturation image generator 106, which corresponds to the oxygen saturation image generator 46, is provided in the capsule endoscope 100. The oxygen saturation image produced by the oxygen saturation image generator 106 is transmitted to the processor device through the transmission/reception antenna 108. The configuration of the image sensor 104 is similar to that of the image sensor 34 of the above embodiment.

Various changes and modifications are possible in the present invention and may be understood to be within the present invention.

What is claimed is:

1. An endoscope system comprising:
    a light source device including:
        a blue light source for emitting blue light having a peak wavelength within a range of 450 to 460 nm;
        a first band limiter having a first transmission band that is defined as a passband where transmittance of the first band limiter is greater than or equal to half a peak value of the transmittance of the first band limiter, the first transmission band including a peak wavelength, at which an absorption coefficient of hemoglobin is at a peak;
        a second band limiter having a second transmission band that is defined as a passband where transmittance of the second band limiter is greater than or equal to half a peak value of the transmittance of the second band limiter, the second transmission band not including an isosbestic wavelength in the order of 450 nm, at which an absorption coefficient of oxyhemoglobin equals an absorption coefficient of deoxyhemoglobin; and
        a controller for selectively switching the first band limiter and the second band limiter;
    an image sensor for imaging an object of interest illuminated by the light source device to output an image signal; and
    a processor configured to produce an image based on the image signal,
    wherein the first transmission band is on a shorter wavelength side than the second transmission band,
    wherein the first transmission band is wider than the second transmission band and partially overlaps with the second transmission band,
    wherein the endoscope system is configured to execute a normal observation using an image in which blood vessel contrast is enhanced, and an observation of oxygen saturation levels,
    wherein the controller is configured to place the first band limiter in a light path of the blue light in the normal observation to generate first blue light in which intensity of the blue light in a wavelength range of greater than or equal to the peak wavelength of the blue light is reduced, and
    wherein the controller is configured to place the second band limiter in the light path of the blue light in the observation of the oxygen saturation levels to generate second blue light in which intensity of the blue light in a wavelength range of less than or equal to the peak wavelength of the blue light is reduced.

2. The endoscope system according to claim 1, the light source device further comprising an optical filter having the first band limiter and the second band limiter, wherein the controller moves the optical filter to place one of the first and second band limiters in the light path of the blue light.

3. The endoscope system according to claim 1, the light source device further comprising:
    a green light source for emitting green light;
    a red light source for emitting red light; and
    a light source controller for generating first illumination light containing the first blue light, the green light, and the red light, and for generating second illumination light containing the second blue light.

4. The endoscope system according to claim 3; wherein the image sensor images an object of interest irradiated with the first or second illumination light and outputs an image signal; and
    the processor is further configured to produce a first image based on the image signal obtained by imaging the object of interest irradiated with the first illumination light and for producing a second image based on the image signal obtained by imaging the object of interest irradiated with the second illumination light.

5. The endoscope system according to claim 4, further comprising a display for displaying the first image and the second image, the display displaying the first and second images simultaneously.

6. The endoscope system according to claim 4, wherein the second blue light has a wavelength range in which the absorption coefficient of oxyhemoglobin is greater than the absorption coefficient of deoxyhemoglobin.

7. The endoscope system according to claim 6, wherein the image sensor has blue pixels for receiving the blue light, green pixels for receiving the green light, and red pixels for receiving the red light.

8. The endoscope system according to claim 7, wherein the processor is further configured to image the object of interest irradiated with the first illumination light and produces the first image based on a first blue image signal outputted from the blue pixels, a first green image signal outputted from the green pixels, and a first red image signal outputted from the red pixels.

9. The endoscope system according to claim 8, wherein the second illumination light is separated into normal light and measurement light, the normal light containing the second blue light, the green light, and the red light, the measurement light being composed of the second blue light, and the processor images the object of interest irradiated with the normal light and produces a base image based on a second blue image signal outputted from the blue pixels, a second green image signal outputted from the green pixels, and a second red image signal outputted from the red pixels, and images the object of interest irradiated with the measurement light and calculates the oxygen saturation level based on a third blue image signal outputted from the blue pixels, and performs image processing of the base image in accordance with the oxygen saturation level to produce the second image.

10. The endoscope system according to claim 7, further comprising a violet light source for emitting violet light to which the blue pixels are sensitive, wherein the light source controller generates the first illumination light containing the violet light, the first blue light, the green light, and the red light.

11. The endoscope system according to claim 4, wherein the endoscope system is capable of executing a normal mode in which the object of interest is irradiated only with the first illumination light and only the first image is produced.

12. The light source device according to claim 1, wherein the peak wavelength of the blue light is 460 nm.

* * * * *